US011826439B2

(12) United States Patent
Lim et al.

(10) Patent No.: US 11,826,439 B2
(45) Date of Patent: Nov. 28, 2023

(54) DISSOLVABLE SOLID ARTICLE CONTAINING ANTI-BACTERIAL ACTIVES

(71) Applicant: The Procter & Gamble Company, Cincinnati, OH (US)

(72) Inventors: Ian-Ling Lim, Singapore (SG); Kai Wei Kelvin Lee, Singapore (SG); Shikhar Gupta, Singapore (SG); Minoru Kobayashi, Singapore (SG); Toshiyuki Okada, Singapore (SG); Robert Wayne Glenn, Jr., Singapore (SG); ChinXin Woo, Singapore (SG)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 17/471,888

(22) Filed: Sep. 10, 2021

(65) Prior Publication Data
US 2022/0071857 A1   Mar. 10, 2022

Related U.S. Application Data

(60) Provisional application No. 63/076,393, filed on Sep. 10, 2020.

(51) Int. Cl.
*A61K 8/02* (2006.01)
*A61K 8/44* (2006.01)
*A61Q 17/00* (2006.01)

(52) U.S. Cl.
CPC .......... *A61K 8/0245* (2013.01); *A61K 8/0216* (2013.01); *A61K 8/44* (2013.01); *A61Q 17/005* (2013.01); *A61K 2800/51* (2013.01)

(58) Field of Classification Search
CPC ........ A01N 25/10; A01N 37/10; A01N 37/40; A01P 1/00; A61K 8/0245; A61K 8/0216; A61K 8/44; A61K 2800/51; A61Q 17/005
See application file for complete search history.

(56) References Cited

U.S. PATENT DOCUMENTS

| | | |
|---|---|---|
| 1,421,350 A | 6/1922 | Powell |
| 2,356,168 A | 8/1944 | Mabley |
| 2,396,278 A | 3/1946 | Otto |
| 2,438,091 A | 3/1948 | Lynch |
| 2,486,921 A | 11/1949 | Byerly |
| 2,486,922 A | 11/1949 | Bruce |
| 2,528,378 A | 10/1950 | Mannheimer |
| 2,658,072 A | 11/1953 | Milton |
| 2,694,668 A | 11/1954 | Fricke |
| 2,809,971 A | 10/1957 | Jack et al. |
| 3,152,046 A | 10/1964 | Maria |
| 3,236,733 A | 2/1966 | Karsten et al. |
| 3,321,425 A | 5/1967 | Karl-ludwig et al. |
| 3,332,880 A | 7/1967 | Adriaan et al. |
| 3,426,440 A | 2/1969 | Shen et al. |
| 3,489,688 A | 1/1970 | Pospischil |
| 3,570,122 A | 3/1971 | Willimas |
| 3,589,007 A | 6/1971 | Walton |
| 3,653,383 A | 4/1972 | Wise |
| 3,695,989 A | 10/1972 | Albert |
| 3,753,196 A | 8/1973 | Kurtz et al. |
| 3,761,418 A | 9/1973 | Parran |
| 3,929,678 A | 12/1975 | Laughlin |
| 3,967,921 A | 7/1976 | Haberli et al. |
| 4,020,156 A | 4/1977 | Murray et al. |
| 4,024,078 A | 5/1977 | Gilbert et al. |
| 4,051,081 A | 9/1977 | Jabs et al. |
| 4,089,945 A | 5/1978 | Brinkman et al. |
| 4,196,190 A | 4/1980 | Gehman et al. |
| 4,197,865 A | 4/1980 | Jacquet et al. |

(Continued)

FOREIGN PATENT DOCUMENTS

| | | |
|---|---|---|
| CN | 1138091 | 12/1996 |
| CN | 1219388 | 6/1999 |

(Continued)

OTHER PUBLICATIONS

AA01427 PCT Search Report and Written Opinion for PCT/US2021/071386 dated Dec. 9, 2021, 11 pages.
All Office Actions; U.S. Appl. No. 12/424,812, filed Apr. 16, 2009.
All Office Actions; U.S. Appl. No. 12/633,228, filed Dec. 8, 2009.
All Office Actions; U.S. Appl. No. 12/633,257, filed Dec. 8, 2009.
All Office Actions; U.S. Appl. No. 12/633,301, filed Dec. 8, 2009.
All Office Actions; U.S. Appl. No. 12/633,335, filed Dec. 8, 2009.
All Office Actions; U.S. Appl. No. 12/633,415, filed Dec. 8, 2009.
All Office Actions; U.S. Appl. No. 12/633,550, filed Dec. 8, 2009.
All Office Actions; U.S. Appl. No. 13/561,298, filed Jul. 30, 2012.
All Office Actions; U.S. Appl. No. 13/597,539, filed Aug. 29, 2012.
All Office Actions; U.S. Appl. No. 13/915,797, filed Jun. 12, 2013.
Anonymous "P8136 Poly(vinyl alcohol)" Internet article, [Online] XP002538935, Retrieved from the Internet: URL:hllp/20 NWW.sigmaaldrich.com/catalog/ProductDetail.do?D7=0%N25-SEARCH_ CONCAT PNOIBRAND KEY%N4=P8136%7SCIAL%N25=0%QS=ON%F=SPEC retrieved on Jul. 28, 2009, year 2009, 1 pg.

(Continued)

*Primary Examiner* — Isaac Shomer
*Assistant Examiner* — Amanda Michelle Petritsch
(74) *Attorney, Agent, or Firm* — Alexandra S. Anoff

(57) ABSTRACT

Disclosed is a dissolvable solid article, comprising by weight of the article: from about 10% to about 50% of a water soluble polymer; from about 20% to about 80% of a surfactant; from about 0.5% to about 2% of diaminocarboxylic acid chelants and salts thereof having an average molecular weight in acid form of from about 250 to about 450 daltons and having a weighted log P value at pH 4 of from about −12 to about −7; from about 0.1% to about 6% of an aromatic carboxylic acid and salts thereof having an average molecular weight in acid form of from about 100 to about 400 daltons and having a weighted log P value at pH 4 of from about −2 to about 4; from about 0.1% to about 18% of an non-aromatic organic alpha hydroxy acid and salts thereof; wherein the dissolvable solid article has a pH of from about 3 to about 5.1 when dissolved with 30 parts water to 1 part of the dissolvable solid article. The present invention provides dissolvable solid articles which provide anti-bacterial benefit even after dissolution of the articles, while controlling the concentration of anti-bacterial active ingredients in the solid articles.

15 Claims, No Drawings

(56) References Cited

U.S. PATENT DOCUMENTS

| | | |
|---|---|---|
| 4,217,914 A | 8/1980 | Jacquet et al. |
| 4,272,511 A | 6/1981 | Papantoniou et al. |
| 4,323,683 A | 4/1982 | Bolich, Jr. et al. |
| 4,345,080 A | 8/1982 | Bolich, Jr. |
| 4,379,753 A | 4/1983 | Bolich, Jr. |
| D269,067 S | 5/1983 | Ballereaud |
| 4,381,919 A | 5/1983 | Jacquet et al. |
| 4,422,853 A | 12/1983 | Jacquet et al. |
| 4,470,982 A | 9/1984 | Winkler |
| 4,507,280 A | 3/1985 | Pohl et al. |
| 4,529,586 A | 7/1985 | De Marco et al. |
| 4,663,158 A | 5/1987 | Wolfram et al. |
| 4,710,374 A | 12/1987 | Grollier et al. |
| 4,723,362 A | 2/1988 | Boerger |
| 4,822,613 A | 4/1989 | Rodero |
| 4,885,107 A | 12/1989 | Wetzel |
| 4,976,953 A | 12/1990 | Orr et al. |
| 4,990,280 A | 2/1991 | Thorengaard |
| 5,055,384 A | 10/1991 | Kuehnert |
| 5,061,481 A | 10/1991 | Suzuki et al. |
| 5,062,889 A | 11/1991 | Hoehl et al. |
| 5,094,853 A | 3/1992 | Hagarty |
| 5,100,657 A | 3/1992 | Ansher-jackson et al. |
| 5,100,658 A | 3/1992 | Bolich, Jr. et al. |
| 5,104,646 A | 4/1992 | Bolich, Jr. |
| 5,106,609 A | 4/1992 | Bolich, Jr. |
| 5,166,276 A | 11/1992 | Hayama et al. |
| 5,220,033 A | 6/1993 | Kamei et al. |
| 5,280,079 A | 1/1994 | Allen et al. |
| RE34,584 E | 4/1994 | Grote et al. |
| 4,565,647 B1 | 4/1994 | Llenado |
| 5,391,368 A | 2/1995 | Gerstein |
| 5,409,703 A | 4/1995 | Mcanalley et al. |
| 5,429,628 A | 7/1995 | Trinh et al. |
| 5,457,895 A | 10/1995 | Thompson et al. |
| 5,476,597 A | 12/1995 | Sakata et al. |
| 5,580,481 A | 12/1996 | Sakata et al. |
| 5,582,786 A | 12/1996 | Brunskill et al. |
| 5,660,845 A | 8/1997 | Trinh et al. |
| 5,672,576 A | 9/1997 | Behrens et al. |
| 5,674,478 A | 10/1997 | Dodd |
| 5,750,122 A | 5/1998 | Evans |
| 5,780,047 A | 7/1998 | Kamiya et al. |
| 5,837,661 A | 11/1998 | Evans et al. |
| 5,932,203 A | 8/1999 | Coffindaffer et al. |
| 5,935,561 A | 8/1999 | Inman et al. |
| 5,955,419 A | 9/1999 | Barket, Jr. et al. |
| 6,010,719 A | 1/2000 | Remon et al. |
| 6,106,849 A | 8/2000 | Malkan et al. |
| 6,177,391 B1 | 1/2001 | Zafar |
| 6,200,949 B1 | 3/2001 | Reijmer et al. |
| 6,458,754 B1 | 10/2002 | Velazquez et al. |
| 6,503,521 B1 | 1/2003 | Atis et al. |
| 6,790,814 B1 | 9/2004 | Marin |
| 6,846,784 B2 | 1/2005 | Engel et al. |
| 6,943,200 B1 | 9/2005 | Corrand et al. |
| 7,015,181 B2 | 3/2006 | Lambino |
| 7,285,520 B2 | 10/2007 | Krzysik |
| D594,752 S | 6/2009 | Medema et al. |
| D613,177 S | 4/2010 | Lee |
| 7,901,696 B2 | 3/2011 | Eknoian et al. |
| D663,631 S | 7/2012 | Mcdermott et al. |
| 8,268,764 B2 | 9/2012 | Glenn, Jr. et al. |
| 8,273,333 B2 | 9/2012 | Glenn, Jr. et al. |
| 8,288,332 B2 | 10/2012 | Fossum et al. |
| 8,309,505 B2 | 11/2012 | Fossum et al. |
| 8,349,341 B2 | 1/2013 | Glenn, Jr. et al. |
| 8,349,786 B2 | 1/2013 | Glenn, Jr. et al. |
| 8,349,787 B2 | 1/2013 | Glenn, Jr. et al. |
| 8,367,596 B2 | 2/2013 | Fossum et al. |
| 8,415,287 B2 | 4/2013 | Glenn, Jr. et al. |
| 8,461,090 B2 | 6/2013 | Glenn, Jr. et al. |
| 8,461,091 B2 | 6/2013 | Glenn, Jr. et al. |
| 8,466,099 B2 | 6/2013 | Glenn, Jr. et al. |
| 8,476,211 B2 | 7/2013 | Glenn, Jr. et al. |
| D695,132 S | 12/2013 | Bouthillon |
| 8,628,706 B2 | 1/2014 | Glenn, Jr. et al. |
| D705,663 S | 5/2014 | Guichot |
| D709,652 S | 7/2014 | Teller |
| 9,295,859 B2 | 3/2016 | Glenn, Jr. |
| D796,964 S | 9/2017 | Staab |
| 9,855,203 B2 | 1/2018 | Mcconaughy et al. |
| 9,867,762 B2 | 1/2018 | Lynch et al. |
| D816,506 S | 5/2018 | Jones et al. |
| 10,149,910 B2 | 12/2018 | Scavone et al. |
| D852,052 S | 6/2019 | Dalton |
| 10,315,838 B1 | 6/2019 | Bishara |
| D878,913 S | 3/2020 | Castellanos et al. |
| D918,054 S | 5/2021 | Papiernik |
| D922,880 S | 6/2021 | Markoulis et al. |
| D928,624 S | 8/2021 | Lim |
| D935,324 S | 11/2021 | Bodum |
| D936,481 S | 11/2021 | Newell |
| D936,483 S | 11/2021 | Xie |
| D946,408 S | 3/2022 | Mainguené |
| 2002/0064510 A1 | 5/2002 | Dalrymple et al. |
| 2002/0077264 A1 | 6/2002 | Roberts et al. |
| 2002/0081930 A1 | 6/2002 | Jackson et al. |
| 2002/0098994 A1 | 7/2002 | Zafar |
| 2002/0099109 A1 | 7/2002 | Dufton et al. |
| 2002/0177621 A1 | 11/2002 | Hanada et al. |
| 2002/0187181 A1 | 12/2002 | Godbey et al. |
| 2003/0032573 A1 | 2/2003 | Tanner et al. |
| 2003/0045441 A1 | 3/2003 | Hsu et al. |
| 2003/0069154 A1 | 4/2003 | Hsu et al. |
| 2003/0080150 A1 | 5/2003 | Cowan et al. |
| 2003/0099691 A1 | 5/2003 | Lydzinski et al. |
| 2003/0099692 A1 | 5/2003 | Lydzinski et al. |
| 2003/0166489 A1 | 9/2003 | Van Asten et al. |
| 2003/0180242 A1 | 9/2003 | Eccard et al. |
| 2003/0186826 A1 | 10/2003 | Eccard et al. |
| 2003/0194416 A1 | 10/2003 | Shefer |
| 2003/0199412 A1 | 10/2003 | Gupta |
| 2003/0207776 A1 | 11/2003 | Shefer et al. |
| 2003/0215522 A1 | 11/2003 | Johnson et al. |
| 2003/0232183 A1 | 12/2003 | Dufton |
| 2004/0029762 A1 | 2/2004 | Hensley |
| 2004/0032859 A1 | 2/2004 | Miao |
| 2004/0048759 A1 | 3/2004 | Ribble et al. |
| 2004/0053808 A1 | 3/2004 | Raehse et al. |
| 2004/0071742 A1 | 4/2004 | Popplewell |
| 2004/0071755 A1 | 4/2004 | Fox |
| 2004/0108615 A1 | 6/2004 | Foley |
| 2004/0110656 A1 | 6/2004 | Casey et al. |
| 2004/0126585 A1 | 7/2004 | Kerins et al. |
| 2004/0175404 A1 | 9/2004 | Shefer |
| 2004/0202632 A1 | 10/2004 | Gott et al. |
| 2004/0206270 A1 | 10/2004 | Vanmaele et al. |
| 2004/0242772 A1 | 12/2004 | Huth et al. |
| 2005/0069575 A1 | 3/2005 | Fox |
| 2005/0118237 A1 | 6/2005 | Krzysik et al. |
| 2005/0136780 A1 | 6/2005 | Clark et al. |
| 2005/0137272 A1 | 6/2005 | Gaserod |
| 2005/0202992 A1 | 9/2005 | Grandio et al. |
| 2005/0220745 A1 | 10/2005 | Lu |
| 2005/0232954 A1 | 10/2005 | Yoshinari et al. |
| 2005/0272836 A1 | 12/2005 | Yaginuma et al. |
| 2005/0287106 A1 | 12/2005 | Legendre |
| 2006/0002880 A1 | 1/2006 | Peffly et al. |
| 2006/0052263 A1 | 3/2006 | Roreger et al. |
| 2006/0228319 A1 | 10/2006 | Vona, Jr. et al. |
| 2007/0028939 A1 | 2/2007 | Mareri et al. |
| 2007/0149435 A1 | 6/2007 | Koenig et al. |
| 2007/0225388 A1 | 9/2007 | Cooper et al. |
| 2008/0035174 A1 | 2/2008 | Aubrun-sonneville |
| 2008/0090939 A1 | 4/2008 | Netravali et al. |
| 2008/0121655 A1 | 5/2008 | Schultz et al. |
| 2008/0131695 A1 | 6/2008 | Aouad et al. |
| 2008/0138492 A1 | 6/2008 | Cingotti |
| 2008/0152894 A1 | 6/2008 | Beihoffer et al. |
| 2008/0215023 A1 | 9/2008 | Scavone et al. |
| 2008/0292669 A1 | 11/2008 | Deng et al. |
| 2008/0293839 A1 | 11/2008 | Stobby |
| 2009/0232873 A1 | 9/2009 | Glenn, Jr. et al. |

(56) References Cited

U.S. PATENT DOCUMENTS

| | | | |
|---|---|---|---|
| 2009/0263342 A1 | 10/2009 | Glenn, Jr. et al. | |
| 2010/0167971 A1 | 7/2010 | Glenn, Jr. et al. | |
| 2010/0173817 A1 | 7/2010 | Glenn, Jr. et al. | |
| 2010/0179083 A1 | 7/2010 | Glenn, Jr. et al. | |
| 2010/0279905 A1 | 11/2010 | Glenn, Jr. | |
| 2010/0286011 A1* | 11/2010 | Glenn, Jr. | A61K 8/0216 510/455 |
| 2010/0291165 A1 | 11/2010 | Glenn, Jr. et al. | |
| 2011/0023240 A1 | 2/2011 | Fossum | |
| 2011/0027328 A1 | 2/2011 | Baig et al. | |
| 2011/0028373 A1* | 2/2011 | Fossum | C11D 17/00 510/236 |
| 2011/0028374 A1 | 2/2011 | Fossum et al. | |
| 2011/0182956 A1 | 7/2011 | Glenn, Jr. et al. | |
| 2011/0189246 A1 | 8/2011 | Glenn, Jr. et al. | |
| 2011/0189247 A1 | 8/2011 | Glenn, Jr. et al. | |
| 2011/0195098 A1 | 8/2011 | Glenn, Jr. et al. | |
| 2011/0240064 A1* | 10/2011 | Wales | C09D 7/65 428/116 |
| 2012/0021026 A1 | 1/2012 | Glenn, Jr. | |
| 2012/0270029 A1 | 10/2012 | Glenn, Jr. et al. | |
| 2013/0115185 A1 | 5/2013 | Tamareselvy et al. | |
| 2013/0303419 A1 | 11/2013 | Glenn, Jr. et al. | |
| 2014/0065077 A1 | 3/2014 | Hollander et al. | |
| 2014/0105946 A1 | 4/2014 | Glenn, Jr. et al. | |
| 2014/0271745 A1 | 9/2014 | Glenn, Jr. et al. | |
| 2015/0313804 A1 | 11/2015 | Lynch et al. | |
| 2015/0313806 A1 | 11/2015 | Lynch et al. | |
| 2015/0313807 A1 | 11/2015 | Lynch et al. | |
| 2015/0313808 A1 | 11/2015 | Lynch et al. | |
| 2015/0313809 A1 | 11/2015 | Lynch et al. | |
| 2018/0216287 A1 | 8/2018 | Weisman | |
| 2018/0216288 A1 | 8/2018 | Weisman et al. | |
| 2018/0333339 A1 | 11/2018 | Hamersky | |
| 2019/0282461 A1 | 9/2019 | Glassmeyer et al. | |
| 2019/0350819 A1 | 11/2019 | Hamersky et al. | |
| 2020/0405587 A1 | 12/2020 | Song | |
| 2021/0094744 A1 | 4/2021 | Benson et al. | |
| 2021/0107263 A1 | 4/2021 | Bartolucci et al. | |
| 2021/0261892 A1 | 8/2021 | Xu et al. | |
| 2021/0354901 A1 | 11/2021 | Glenn, Jr. et al. | |
| 2021/0354902 A1 | 11/2021 | Cheng et al. | |
| 2021/0354903 A1 | 11/2021 | Glenn, Jr. et al. | |
| 2022/0204243 A1 | 6/2022 | MacNamara et al. | |

FOREIGN PATENT DOCUMENTS

| | | | |
|---|---|---|---|
| CN | 1268558 | | 10/2000 |
| CN | 1357613 | A | 7/2002 |
| CN | 1454231 | A | 11/2003 |
| CN | 1530431 | A | 9/2004 |
| CN | 1583991 | A | 2/2005 |
| CN | 1726074 | A | 1/2006 |
| CN | 105087173 | A | 11/2015 |
| DE | 19607851 | A1 | 9/1997 |
| DE | 10331767 | A1 | 2/2005 |
| EP | 0392608 | A2 | 10/1990 |
| EP | 609808 | A1 | 8/1994 |
| EP | 0858828 | A1 | 8/1998 |
| EP | 0948960 | A2 | 10/1999 |
| EP | 1214879 | A2 | 6/2002 |
| EP | 1317916 | A2 | 6/2003 |
| EP | 1217987 | B1 | 12/2004 |
| EP | 1574561 | A1 | 9/2005 |
| EP | 1160311 | B1 | 3/2006 |
| EP | 2085434 | A1 | 8/2009 |
| EP | 2529927 | A2 | 12/2012 |
| EP | 3326696 | A1 * | 5/2018 ........... A61K 8/0233 |
| FR | 2871685 | A1 | 12/2005 |
| FR | 2886845 | A1 | 12/2006 |
| GB | 2235204 | A | 2/1991 |
| GB | 2355008 | A | 4/2001 |
| GB | 2378407 | A | 2/2003 |
| JP | 5802160 | | 2/1983 |
| JP | S58216109 | A | 12/1983 |
| JP | S6272609 | A | 4/1987 |
| JP | S6272610 | A | 4/1987 |
| JP | S6281432 | A | 4/1987 |
| JP | H01313418 | A | 12/1989 |
| JP | H05344873 | A | 12/1993 |
| JP | H0617083 | A | 1/1994 |
| JP | H0789852 | A | 4/1995 |
| JP | H08325133 | A | 12/1996 |
| JP | H10251371 | A | 9/1998 |
| JP | H11513053 | A | 11/1999 |
| JP | 2000229841 | A | 8/2000 |
| JP | 2001519376 | A | 10/2001 |
| JP | 2001520983 | A | 11/2001 |
| JP | 2002226895 | A | 8/2002 |
| JP | 2003073700 | A | 3/2003 |
| JP | 2003082397 | A | 3/2003 |
| JP | 2004509198 | A | 3/2004 |
| JP | 2004345983 | A | 12/2004 |
| JP | 2005171063 | A | 6/2005 |
| JP | 2005538202 | A | 12/2005 |
| JP | 2006056835 | A | 3/2006 |
| JP | 2007001889 | A | 1/2007 |
| JP | 2007091954 | A | 4/2007 |
| JP | 2007197365 | A | 8/2007 |
| JP | 2007197540 | A | 8/2007 |
| JP | 2012511050 | A | 5/2012 |
| JP | 2017008265 | A | 1/2017 |
| JP | 2017519811 | A | 7/2017 |
| JP | 2019177039 | A | 10/2019 |
| JP | 1701938 | S | 12/2021 |
| JP | 1704689 | S | 1/2022 |
| KR | 20020003442 | A | 1/2002 |
| WO | 9514495 | A1 | 6/1995 |
| WO | 9951715 | A1 | 10/1999 |
| WO | 0042992 | A2 | 7/2000 |
| WO | 0107194 | A1 | 2/2001 |
| WO | 0124779 | A1 | 4/2001 |
| WO | 0125322 | A1 | 4/2001 |
| WO | 0125393 | A1 | 4/2001 |
| WO | 2001024770 | A1 | 4/2001 |
| WO | 2004032859 | A1 | 4/2004 |
| WO | 2004041991 | A1 | 5/2004 |
| WO | 2005003423 | A1 | 1/2005 |
| WO | 2007033598 | A1 | 3/2007 |
| WO | 2007093558 | A1 | 8/2007 |
| WO | 2007102119 | A1 | 9/2007 |
| WO | 2008104954 | A2 | 9/2008 |
| WO | 2009019571 | A2 | 2/2009 |
| WO | 2012167368 | A1 | 12/2012 |
| WO | 2018140675 | A1 | 8/2018 |
| WO | 2018140676 | A2 | 8/2018 |
| WO | 2020264574 | A1 | 12/2020 |
| WO | 2022056624 | A1 | 3/2022 |

OTHER PUBLICATIONS

Database GNPD, Mintel; Anonymous: "2 in 1 Dandruff ShampoobrFormulation", May 5, 2004, 2 Pages.

Database WPI Week 201617 Thomson Scientific, London, GB; AN 2015-81043C 71002806297, & CN 105 087 173 A (Zhoushan Sunlight Marine Technology Co) Nov. 25, 2015 (Nov. 25, 2015) abstract example 1.

Elegant Square Acrylic Cosmetic Refillable Cream Jar (30g) Online, published date unknown. Retrieved on Apr. 15, 2022, 1 pg.from URL: https://www.fasttech.com/product/9683542-elegant-square-acrylic-cosmetic-refillable-cream.

Encyclopedia of Polymer Science and Engineering, vol. 15, 2nd ed., pp. 204 308 Silicones, year 1989.

Foaming Shampoo Dispenser Bottle, Sureaam 4 Pack 8.45oz/250ml Blue Plastic Refillable Hand Pump Container for Lotion, Conditioner, Empty Small Square Bottle for Bathroom Body Wash, Kitchen Sink, Travel Online, published date unknown. Retrievedon Apr. 15, 2022, 1 pg. URL: https://www.ubuy.co.id/en/product/D14CVKA-foamin.

(56) References Cited

OTHER PUBLICATIONS

Hildebrand, T., et al. "Quantification of bone microarchitecture with the structure mode index", Computer Methods in Biomechanics and Biomedical Engineering, vol. 1, Jan. 14, 1997, pp. 15-23.

Hiroshi Yagi & 4 Others, Research Study of a Friction Protector for Preventing a Tow Line From Breaking, Working Papers for Fiscal 2006 | Japan | Japan Coast Guard Dec. 2007, pp. 1-8.

Latorre Carmen, Nanotribological Effects of Hair Careproducts and Environment on Human Hair Using Atomic Forcemicroscopy,Journal of Vacuum Science and Technology: Part A, U.S.A, AVS/AIP , Jun. 28, 2005 , V2 3 N 4, p. 1034-1045.

Vaughan, C.D. "Solubility, Effects in Product, Package, Penetration and Preservation", Cosmetics and Toiletries, vol. 103, Oct. 1988, 24 pgs.

Vesterby, A.: "Star vol. in Bone Research: A Histomorphometric Analysis Of Trabecular Bone Structure Using Vertical Sections", Anal Rec: Feb. 1993, 232(2), pp. 325-334.

\* cited by examiner

DISSOLVABLE SOLID ARTICLE CONTAINING ANTI-BACTERIAL ACTIVES

FIELD OF THE INVENTION

The present invention relates to a dissolvable solid article, comprising by weight of the article: from about 10% to about 50% of a water soluble polymer; from about 20% to about 80% of a surfactant; from about 0.5% to about 2% of diaminocarboxylic acid chelants and salts thereof having an average molecular weight in acid form of from about 250 to about 450 daltons and having a weighted log P value at pH 4 of from about −12 to about −7; from about 0.1% to about 6% of an aromatic carboxylic acid and salts thereof having an average molecular weight in acid form of from about 100 to about 400 daltons and having a weighted log P value at pH 4 of from about −2 to about 4; from about 0.1% to about 18% of an non-aromatic organic alpha hydroxy acid and salts thereof; wherein the dissolvable solid article has a pH of from about 3 to about 5.1 when dissolved with 30 parts water to 1 part of the dissolvable solid article. The present invention provides dissolvable solid articles which provide anti-bacterial benefit even after dissolution of the articles, while controlling the concentration of anti-bacterial active ingredients in the solid articles.

BACKGROUND OF THE INVENTION

Flexible and dissolvable solid articles comprising surfactant(s) and/or other active ingredients in a water-soluble polymeric carrier or matrix are well known. Such articles are particularly useful for delivering surfactants and/or other active ingredients upon dissolution in water. In comparison with traditional granular or liquid forms in the same product category, such articles have better structural integrity, are more concentrated and easier to store, ship/transport, carry, and handle. In comparison with the solid tablet form in the same product category, such articles can provide faster dissolution and/or more aesthetic appeal to the consumers.

Such dissolvable solid articles are generally used by dissolving the articles with, for example, 10-30 parts of water to 1 part of the article water. The concentration of ingredients contained in the articles are diluted during and after dissolution. There exists a need for dissolvable solid articles to provide anti-bacterial benefit to the applied substrate, for example, skin and/or hair when the articles are personal care products. However, when containing an anti-bacterial active ingredient at a level enough to provide anti-bacterial benefit after dissolution of the solid article, the concentration of such active ingredient becomes too high in the solid articles before dissolution. Some country's regulations require an upper limitation of the concentration of such anti-bacterial active ingredient in the article before dissolution.

Therefore, there is a need for dissolvable solid articles which provide anti-bacterial benefit even after dissolution of the article, while controlling the concentration of anti-bacterial active ingredient in the solid articles.

SUMMARY OF THE INVENTION

The present invention is directed to a dissolvable solid article, comprising by weight of the article:
 a. from about 10% to about 50% of a water soluble polymer;
 b. from about 20% to about 80% of a surfactant;
 c. from about 0.5% to about 2% of diaminocarboxylic acid chelants and salts thereof having an average molecular weight in acid form of from about 250 to about 450 daltons and having a weighted log P value at pH 4 of from about −12 to about −7;
 d. from about 0.1% to about 6% of an aromatic carboxylic acid and salts thereof having an average molecular weight in acid form of from about 100 to about 400 daltons and having a weighted log P value at pH 4 of from about −2 to about 4;
 e. from about 0.1% to about 18% of a non-aromatic organic alpha hydroxy acid and salts thereof;
 wherein the dissolvable solid article has a pH of from about 3 to about 5.1 when dissolved with 30 parts water to 1 part of the dissolvable solid article.

In one embodiment, the dissolvable solid article of the above feature has a pH of from about 3.5 to about 4.9 when dissolved with 30 parts water to 1 part of the dissolvable solid article.

In one embodiment, the dissolvable solid article of any of the above features has a pH of from about 3.8 to about 4.8 when dissolved with 30 parts water to 1 part of the dissolvable solid article.

In one embodiment, the dissolvable solid article of any of the above features further comprises from about 0.1% to about 2.0% of a diol having an average molecular weight of from about 90 to about 500 daltons and a weighted log P value at pH 4 of from about −1 to about 12.

In one embodiment, the dissolvable solid article of any of the above features comprises two or more flexible, dissolvable, porous sheets.

In one embodiment, the dissolvable solid article of any of the above features has a density ranging from about 0.050 g/cm$^3$ to about 0.380 g/cm$^3$.

The present invention provides dissolvable solid articles which provide anti-bacterial benefit even after dissolution of the articles, while controlling the concentration of anti-bacterial active ingredients in the solid articles. By the combination of specific anti-bacterial active ingredients and the use of such combination at a specific pH, it becomes possible to provide anti-bacterial benefit even after dissolution of the articles, while controlling the concentration of each anti-bacterial active ingredient in the solid articles.

These and other aspects of the present invention will become more apparent upon reading the following detailed description of the invention.

DETAILED DESCRIPTION OF THE INVENTION

While the specification concludes with claims particularly pointing out and distinctly claiming the invention, it is believed that the present invention will be better understood from the following description.

Herein, "comprising" means that other steps and other ingredients which do not affect the end result can be added. This term encompasses the terms "consisting of" and "consisting essentially of".

All percentages, parts and ratios are based upon the total weight of the compositions of the present invention, unless otherwise specified. All such weights as they pertain to listed ingredients are based on the active level and, therefore, do not include carriers or by-products that may be included in commercially available materials.

Herein, "mixtures" is meant to include a simple combination of materials and any compounds that may result from their combination.

The term "molecular weight" or "M.Wt." as used herein refers to the weight average molecular weight unless otherwise stated. The weight average molecular weight may be measured by gel permeation chromatography.

"QS" means sufficient quantity for 100%.

Diaminocarboxylic Acid Chelant

The dissolvable solid article of the present invention comprises diaminocarboxylic acid chelants and salts thereof. The diaminocarboxylic acid chelants and salts thereof are included in the article at a level of from about 0.5% to about 2%, alternatively from about 0.75% to about 1.5%, by weight of the article.

The diaminocarboxylic acid chelants and salts thereof useful herein are those having an average molecular weight (in acid form) of from about 250 to about 450 daltons, alternatively from about 250 to 350 daltons, and having a weighted log P value at pH 4 of from about −12 to about −7, from about −10 to about −8.

Such diaminocarboxylic acid chelants include, for example, those in the below table and salts thereof.

|  | LogP at pH4 | MW |
|---|---|---|
| Ethylenediaminetetraacetic acid | −9.312 | 292.24 |
| 2-[3-[bis(carboxymethyl)amino]propyl-(carboxymethyl)amino]acetic acid | −9.864 | 306.27 |
| 1,2-Diaminopropane-N,N,N',N'-tetraacetic acid | −8.945 | 306.27 |
| 1,3-DIAMINO-2-PROPANOL-N,N,N',N'-TETRAACETIC ACID | −10.843 | 322.27 |
| N-(2-Hydroxyethyl)Ethylenediaminetriacetic Acid | −7.486 | 278.26 |
| 2-[2-[2-[bis(carboxymethyl)amino]ethoxy]ethyl-(carboxymethyl)amino]acetic acid | −10.601 | 336.3 |
| 2-[[2-[bis(carboxymethyl)amino]cyclopropyl]-(carboxymethyl)amino]acetic acid | −10.634 | 304.25 |
| pentetic acid | −11.767 | 393.35 |
| 2-[3-[bis(carboxymethyl)amino]butan-2-yl-(carboxymethyl)amino]acetic acid | −8.462 | 320.3 |
| ethylene glycol bis(2-aminoethyl)tetraacetic acid | −10.732 | 380.35 |

Among them, preferred are those in the below table and salts thereof.

|  | LogP at pH4 | MW |
|---|---|---|
| Ethylenediaminetetraacetic acid | −9.312 | 292.24 |
| 2-[3-[bis(carboxymethyl)amino]propyl-(carboxymethyl)amino]acetic acid | −9.864 | 306.27 |
| 1,2-Diaminopropane-N,N,N',N'-tetraacetic acid | −8.945 | 306.27 |
| 1,3-DIAMINO-2-PROPANOL-N,N,N',N'-TETRAACETIC ACID | −10.843 | 322.27 |
| 2-[2-[2-[bis(carboxymethyl)amino]ethoxy]ethyl-(carboxymethyl)amino]acetic acid | −10.601 | 336.3 |

Among them, more preferred is that in the below table and salts thereof.

|  | LogP at pH4 | MW |
|---|---|---|
| Ethylenediaminetetraacetic acid | −9.312 | 292.24 |

Aromatic Carboxylic Acid

The dissolvable solid article of the present invention comprises aromatic carboxylic acids and salts thereof. The aromatic carboxylic acids and salts thereof are included in the article at a level of from about 0.1% to about 6%, alternatively from about 0.2% to about 5%, alternatively from about 0.3% to about 4% by weight of the article.

The aromatic carboxylic acid and salts thereof useful herein are those having an average molecular weight (in acid form) of from about 100 to about 400 daltons, alternatively from about 105 to about 200 daltons, alternatively from about 110 to about 150 daltons, and having a weighted log P value at pH 4 of from about −2 to about 4, from about −0.5 to about 2, alternatively from about 0 to about 1.5.

Such aromatic carboxylic acids include, for example, those in the below table and salts thereof.

|  | LogP at pH4 | MW |
|---|---|---|
| Salicylic acid | 0.289 | 138.1207 |
| Benzoic acid | 0.91 | 122.1213 |
| Hydroxycinnamic Acid | 1.593 | 164.16 |
| Capryloyl Salicylic Acid | 3.27 | 264.32 |
| Orotic Acid | −0.408 | 156.0963 |
| Rosmarinic Acid | 2.535 | 360.3148 |
| Pyridinedicarboxylic Acid | −0.935 | 167.1189 |
| Hydroxyphenyl Propamidobenzoic Acid | 1.171 | 285.2946 |
| Ferulic Acid | 1.571 | 194.184 |
| Chlorogenic Acid | −1.46 | 354.3087 |
| Gallic Acid | 0.573 | 170.1195 |
| P-Anisic Acid | 1.321 | 152.1473 |
| Cinnamic Acid | 1.709 | 148.1586 |
| Usnic Acid | 1.228 | 344.3154 |
| Caffeic Acid | 1.353 | 180.1574 |
| Phthalic Acid | 0.125 | 166.1308 |
| 2,6-Cresotic acid | 1.006 | 152.1473 |
| 2,3-DIHYDROXYBENZOIC ACID | 0.07 | 154.1201 |
| 2,6-DIHYDROXYBENZOIC ACID | −0.478 | 154.1201 |
| 2,4-DIHYDROXYBENZOIC ACID | 0.208 | 154.1201 |
| 4-HYDROXYBENZOIC ACID | 1.125 | 138.1207 |
| 2,5-Cresotic acid | 1.154 | 152.1473 |
| 3 Hydroxyanthranilic acid | −0.729 | 153.1354 |
| Gentisic acid | 0.07 | 154.1201 |
| 2,4-Cresotic acid | 0.902 | 152.1473 |
| 5-AMINO SALICYLIC ACID | −1.191 | 153.1354 |
| Anthranilic acid | −0.71 | 137.136 |

Among them, preferred are those in the below table and salts thereof.

|  | LogP at pH4 | MW |
|---|---|---|
| Salicylic acid (sodium/potassium salicylate) | 0.289 | 138.1207 |
| Benzoic acid (sodium benzoate) | 0.91 | 122.1213 |
| Hydroxycinnamic Acid | 1.593 | 164.16 |
| Capryloyl Salicylic Acid | 3.27 | 264.32 |
| Rosmarinic Acid | 2.535 | 360.3148 |
| Pyridinedicarboxylic Acid | −0.935 | 167.1189 |
| Ferulic Acid | 1.571 | 194.184 |
| Gallic Acid | 0.573 | 170.1195 |
| P-Anisic Acid | 1.321 | 152.1473 |
| Cinnamic Acid | 1.709 | 148.1586 |
| Usnic Acid | 1.228 | 344.3154 |
| Caffeic Acid | 1.353 | 180.1574 |
| Gentisic acid | 0.07 | 154.1201 |

Among them, more preferred are those in the below table and salts thereof.

|  | LogP at pH4 | MW |
|---|---|---|
| Salicylic acid (sodium/potassium salicylate) | 0.289 | 138.1207 |
| Benzoic acid (sodium benzoate) | 0.91 | 122.1213 |

As shown above, aromatic carboxylic acids and salts thereof are alternatively selected from the group consisting of: at least one selected from salicylic acid and salts thereof; at least one selected from benzoic acid and salts thereof; and mixtures thereof, alternatively selected from the mixtures thereof. Salicylic acids and salts thereof can be included in the article at a level of from about 0.1% to about 2.5%, alternatively from about 0.2% to about 2%, alternatively from about 0.3% to about 1.5% by weight of the article. Benzoic acids and salts thereof can be included in the article at a level of from about 0.1% to about 5%, alternatively from about 0.2% to about 3%, alternatively from about 0.3% to about 2.5% by weight of the article.

Non-Aromatic Organic Alpha Hydroxy Acid

The dissolvable solid article of the present invention comprises a non-aromatic organic alpha hydroxy acid (organic AHA) and salts thereof. The non-aromatic organic AHAs and salts thereof are included in the article at a level of from about 0.1% to about 18%, alternatively from about 0.5% to about 12%, alternatively from about 1% to about 6%, still alternatively from 1% to about 4%, and alternatively from about 1% to about 3% by weight of the article.

The organic AHAs useful herein, and include, for example, those in the below table and salts thereof.

| |
| --- |
| Citric acid |
| Lactic acid |
| Malic acid |
| Tartaric acid |
| Gluconic acid |
| Glyceric acid |
| Xylonic acid |
| Galactaric Acid |

Among them, preferred are those in the below table and salts thereof.

| |
| --- |
| Citric acid |
| Lactic acid |
| Gluconic acid |

Among them, more preferred is that in the below table and salts thereof.

| |
| --- |
| Citric acid |

Non-AHA, Non-Aromatic Acid

The dissolvable solid article of the present invention may further comprise a non-AHA, non-aromatic acids and salts thereof. The non-AHA, non-aromatic acids and salts thereof can be included in the article at a level of from about 0.1% to about 10%, alternatively from about 0.1% to about 5%, alternatively from about 0.1% to about 3%, by weight of the article.

The non-AHA, non-aromatic acids useful herein include, for example, those in the below table and salts thereof.

| |
| --- |
| Sorbic acid |
| Succinic acid |
| Phytic acid |
| Acetic acid |
| Malonic acid |
| Fumaric Acid |
| Glyoxylic Acid |
| HCl |

Among them, preferred are organic acids and salts thereof, and more preferred are those in the below table and salts thereof.

| |
| --- |
| Sorbic acid |
| Succinic acid |
| Phytic acid |
| Acetic acid |

Diol

The dissolvable solid article of the present invention may further comprise a diol. The diol can be included in the article at a level of from about 0.1% to about 2%, alternatively from about 0.25% to about 1.5%, by weight of the article.

The diols useful herein are those having an average molecular weight of from about 90 to about 500 daltons, alternatively from about 100 to about 250 daltons, alternatively from about 110 to about 160 daltons, and having a weighted log P value at pH 4 of from about −1 to about 12, from about 0 to about 7, alternatively from about 0.5 to about 4.

Such diols useful herein include, for example, those in the below table.

| | LogP at pH4 | MW |
| --- | --- | --- |
| 1,2-Hexanediol | 0.92 | 118.17 |
| 1,2-Octanediol | 1.83 | 146.23 |
| 1,2-octacosanediol | 10.952 | 426.76 |
| 1,2-octadecanediol | 6.39 | 286.4931 |
| 1,2-hexadecanediol | 5.478 | 258.44 |
| 1,2-tetradecanediol | 4.565 | 230.3868 |
| 1,2-Decanediol | 2.741 | 174.2805 |
| 1,2-Dodecanediol | 3.653 | 202.3336 |
| 1,2-hexacosanediol | 10.04 | 398.71 |
| ARACHIDYL GLYCOL | 7.302 | 314.55 |
| 1,2-Pentanediol | 0.459 | 104.1476 |
| 1,3-Heptanediol | 0.978 | 132.2007 |
| 1,5-Hexanediol | 0.578 | 118.1742 |
| 1,3-Hexanediol | 0.522 | 118.1742 |
| 1,2,6-Hexanetriol | −0.31 | 134.1736 |
| 1-hexanol, 2-amino-5-methyl- | −0.127 | 131.216 |
| 7-Octene-1,2-Diol | 1.437 | 144.21144 |
| 1-Methyl-1-octanol | 3.172 | 144.2545 |
| Octan-2-ol | 2.716 | 130.22792 |
| Nonanol-3 | 3.24 | 144.2545 |

Among them, preferred are those in the below table.

| | LogP at pH4 | MW |
| --- | --- | --- |
| 1,2-Hexanediol | 0.92 | 118.17 |
| 1,2-Octanediol | 1.83 | 146.23 |
| 1,2-octacosanediol | 10.952 | 426.76 |
| 1,2-octadecanediol | 6.39 | 286.4931 |
| 1,2-hexadecanediol | 5.478 | 258.44 |
| 1,2-Decanediol | 2.741 | 174.2805 |
| 1,2-hexacosanediol | 10.04 | 398.71 |
| 1,2-Pentanediol | 0.459 | 104.1476 |
| 1,2,6-Hexanetriol | −0.31 | 134.1736 |
| 7-Octene-1,2-Diol | 1.437 | 144.21144 |

Among them, more preferred are those in the below table.

| | LogP at pH4 | MW |
| --- | --- | --- |
| 1,2-Hexanediol | 0.92 | 118.17 |
| 1,2-Octanediol | 1.83 | 146.23 |

Water-Soluble Polymer ("Polymer Structurant")

The present invention comprises water-soluble polymer that functions as a structurant. The water soluble polymer is included in the article at a level of from about 10% to about 50%, alternatively from about 15% to about 40%, alternatively from about 18% to about 30%, by weight of the article. As used herein, the term "water-soluble polymer" is broad enough to include both water-soluble and water-dispersible polymers, and is defined as a polymer with a solubility in water, measured at 25° C., of at least about 0.1 gram/liter (g/L). In some embodiments, the polymers have a solubility in water, measured at 25° C., of from about 0.1 gram/liter (g/L). to about 500 grams/liter (g/L). (This indicates production of a macroscopically isotropic or transparent, colored or colorless solution). The polymers for making these solids may be of synthetic or natural origin and may be modified by means of chemical reactions. They may or may not be film-forming. These polymers should be physiologically acceptable, i.e., they should be compatible with the skin, mucous membranes, the hair and the scalp.

The terms "water-soluble polymer" and "polymer structurant" are used interchangeably herein. Furthermore, whenever the singular term "polymer" is stated, it should be understood that the term is broad enough to include one polymer or a mixture of more than one polymer. For instance, if a mixture of polymers is used, the polymer solubility as referred to herein would refer to the solubility of the mixture of polymers, rather than to the solubility of each polymer individually.

The one or more water-soluble polymers of the present invention are selected such that their weighted average molecular weight is from about 40,000 to about 500,000, in one embodiment from about 50,000 to about 400,000, in yet another embodiment from about 60,000 to about 300,000, and in still another embodiment from about 70,000 to about 200,000. The weighted average molecular weight is computed by summing the average molecular weights of each polymer raw material multiplied by their respective relative weight percentages by weight of the total weight of polymers present within the porous solid.

A variety of water-soluble polymers can be used in the present invention, as shown below. Among them, highly preferred is polyvinyl alcohols.

The water-soluble polymer(s) of the present invention can include, but are not limited to, synthetic polymers including polyvinyl alcohols, polyvinylpyrrolidones, polyalkylene oxides, polyacrylates, caprolactams, polymethacrylates, polymethylmethacrylates, polyacrylamides, polymethylacrylamides, polydimethylacrylamides, copolymers of acrylic acid and methyl methacrylate, polyethylene glycol monomethacrylates, polyurethanes, polycarboxylic acids, polyvinyl acetates, polyesters, polyamides, polyamines, polyethyleneimines, maleic/(acrylate or methacrylate) copolymers, copolymers of methylvinyl ether and of maleic anhydride, copolymers of vinyl acetate and crotonic acid, copolymers of vinylpyrrolidone and of vinyl acetate, copolymers of vinylpyrrolidone and of caprolactam, vinyl pyrrolidone/vinyl acetate copolymers, copolymers of anionic, cationic and amphoteric monomers, and combinations thereof.

The water-soluble polymer(s) of the present invention may also be selected from naturally sourced polymers including those of plant origin examples of which include karaya gum, tragacanth gum, gum Arabic, acemannan, konjac mannan, acacia gum, gum ghatti, whey protein isolate, and soy protein isolate; seed extracts including guar gum, locust bean gum, quince seed, and psyllium seed; seaweed extracts such as Carrageenan, alginates, and agar; fruit extracts (pectins); those of microbial origin including xanthan gum, gellan gum, pullulan, hyaluronic acid, chondroitin sulfate, and dextran; and those of animal origin including casein, gelatin, keratin, keratin hydrolysates, sulfonic keratins, albumin, collagen, glutelin, glucagons, gluten, zein, and shellac.

Modified natural polymers are also useful as water-soluble polymer(s) in the present invention. Suitable modified natural polymers include, but are not limited to, cellulose derivatives such as hydroxypropylmethylcellulose, hydroxymethylcellulose, hydroxyethylcellulose, methylcellulose, hydroxypropylcellulose, ethylcellulose, carboxymethylcellulose, cellulose acetate phthalate, nitrocellulose and other cellulose ethers/esters; and guar derivatives such as hydroxypropyl guar.

Suitable water-soluble polymers of the present invention include polyvinyl alcohols, polyvinylpyrrolidones, polyalkylene oxides, starch and starch derivatives, pullulan, gelatin, hydroxypropylmethylcelluloses, methycelluloses, and carboxymethycelluloses.

More preferred water-soluble polymers of the present invention include polyvinyl alcohols, and hydroxypropylmethylcelluloses. Suitable polyvinyl alcohols include those available from Celanese Corporation (Dallas, TX) under the Celvol trade name including, but not limited to, Celvol 523, Celvol 530, Celvol 540, Celvol 518, Celvol, 513, Celvol 508, Celvol 504, and combinations thereof. Suitable hydroxypropylmethylcelluloses include those available from the Dow Chemical Company (Midland, MI) under the Methocel trade name including, but not limited, to Methocel E50, Methocel E15, Methocel E6, Methocel E5, Methocel E3, Methocel F50, Methocel K100, Methocel K3, Methocel A400, and combinations thereof including combinations with above mentioned hydroxypropylmethylcelluloses.

Most preferred water-soluble polymers of the present invention are polyvinyl alcohols characterized by a degree of hydrolysis ranging from about 40% to about 100%, alternatively from about 50% to about 95%, alternatively from about 70% to about 92%, alternatively from about 80% to about 90%. Commercially available polyvinyl alcohols include those from Celanese Corporation (Texas, USA) under the CELVOL trade name including, but not limited to, CELVOL 523, CELVOL 530, CELVOL 540, CELVOL 518, CELVOL 513, CELVOL 508, CELVOL 504; those from Kuraray Europe GmbH (Frankfurt, Germany) under the Mowiol® and POVAL™ trade names; and PVA 1788 (also referred to as PVA BP17) commercially available from various suppliers including Lubon Vinylon Co. (Nanjing, China), for example, BP-17 having 86-90% degree of hydrolysis, Approximate MW (weight average)=70,000-120,000 daltons, available from Liwei Chemical Co. Ltd., China; and combinations thereof. In a particularly preferred embodiment of the present invention, the flexible, porous, dissolvable solid sheet article comprises from about 10% to about 25%, alternatively from about 15% to about 23%, by total weight of such article, of a polyvinyl alcohol having a weight average molecular weight ranging from 80,000 to about 150,000 Daltons and a degree of hydrolysis ranging from about 80% to about 90%.

Surfactant

The dissolvable solid article of the present invention comprises a surfactant. The surfactant is included in the article at a level of from about 20% to about 80%, alternatively from about 23% to about 75%, alternatively from about 35% to about 65%, by weight of the article. The surfactant comprises a blend of Group I and Group II surfactants. The blend of surfactants of the present invention comprises one or more surfactants from Group I and one or more surfactants from Group II. Group I surfactants include anionic surfactants, and Group II surfactants include amphoteric surfactants, zwitterionic surfactants, and combinations thereof. In one embodiment of the present invention, the ratio of Group I to Group II surfactants is from about 90:10 to about 55:45. In yet another embodiment of the present invention the ratio of Group I to Group II surfactants is from about 85:15 to about 65:35.

Group I Surfactants

The Group I surfactants of the present invention include one or more anionic surfactants. Suitable anionic surfactant components for use in the Dissolvable Article herein include those which are known for use in hair care or other personal care cleansing compositions. The concentration of the anionic surfactant component in the composition should be sufficient to provide the desired cleaning and lather performance, from about 6.5% to about 71% weight % of dry solids of a Group I surfactant.

Anionic surfactants suitable for use in the compositions include sulfate-free surfactants. Such sulfate-free surfactants can comprise a material derived from an amino acid such as mono and dicarboxylate salts such as glutamate, glycinate, taurate, alaninate or sarcosinate. Examples include sodium lauroyl glutamate, sodium cocoyl glutamate, potassium lauroyl glutamate, sodium cocoyl alaninate, sodium cocoyl glycinate, sodium lauroyl sarcosinate, sodium cocoyl sarcosinate, sodium cocoyl methyl taurate, sodium lauryl methyl isethionate, sodium cocoyl isethionate, or sodium oleoyl sarcosinate.

Anionic surfactants suitable for use in the compositions include alkyl and alkyl ether sulfates. These materials have the respective formulae ROSO3M and RO(C2H4O)xSO3M, wherein R is alkyl or alkenyl of from about 8 to about 18 carbon atoms, x is an integer having a value of from 1 to 10, and M is a cation such as ammonium, alkanolamines, such as triethanolamine, monovalent metals, such as sodium and potassium, and polyvalent metal cations, such as magnesium, and calcium. Alternatively, R has from about 8 to about 18 carbon atoms, alternatively from about 10 to about 16 carbon atoms, even alternatively from about 11 to about 14 carbon atoms, in both the alkyl and alkyl ether sulfates. The alkyl ether sulfates are typically made as condensation products of ethylene oxide and monohydric alcohols having from about 8 to about 24 carbon atoms. The alcohols can be synthetic or they can be derived from fats, e.g., coconut oil, palm kernel oil, tallow. Synthetic alcohols may include the grades available via Shell Chemical Co. under the NEODOL trade name as NEODOL 91 (C9-11 alcohols), NEODOL 23 (C12-13 alcohols), NEODOL 25 (C12-15 alcohols), NEODOL 45 (C14-15 alcohols), and NEODOL 135 (C11-C13-C15 alcohols). Lauryl alcohol and straight chain alcohols derived from coconut oil or palm kernel oil are preferred. Such alcohols are reacted with between about 0 and about 10, in one embodiment from about 2 to about 5, in another embodiment about 3, molar proportions of ethylene oxide, and the resulting mixture of molecular species having, for example, an average of 3 moles of ethylene oxide per mole of alcohol, is sulfated and neutralized.

Other suitable anionic surfactants are the water-soluble salts of organic, sulfuric acid reaction products conforming to the formula [R1-SO3-M] where R1 is a straight or branched chain, saturated, aliphatic hydrocarbon radical having from about 8 to about 24, alternatively about 10 to about 18, carbon atoms; and M is a cation described hereinbefore.

Still other suitable anionic surfactants are the reaction products of fatty acids esterified with isethionic acid and neutralized with sodium hydroxide where, for example, the fatty acids are derived from coconut oil or palm kernel oil; sodium or potassium salts of fatty acid amides of methyl tauride in which the fatty acids, for example, are derived from coconut oil or palm kernel oil. Other similar anionic surfactants are described in U.S. Pat. Nos. 2,486,921; 2,486,922; and 2,396,278.

Other anionic surfactants suitable for use in the compositions are the succinnates, examples of which include disodium N-octadecylsulfosuccinnate; disodium laurylsulfosuccinate; diammonium laurylsulfosuccinate; tetrasodium N-(1,2-dicarboxyethyl)-N-octadecylsulfosuccinnate; diamyl ester of sodium sulfosuccinic acid; dihexyl ester of sodium sulfosuccinic acid; and dioctyl esters of sodium sulfosuccinic acid.

Other suitable anionic surfactants include olefin sulfonates having about 10 to about 24 carbon atoms. In addition to the true alkene sulfonates and a proportion of hydroxy-alkanesulfonates, the olefin sulfonates can contain minor amounts of other materials, such as alkene disulfonates depending upon the reaction conditions, proportion of reactants, the nature of the starting olefins and impurities in the olefin stock and side reactions during the sulfonation process. A non limiting example of such an alpha-olefin sulfonate mixture is described in U.S. Pat. No. 3,332,880.

Another class of anionic surfactants suitable for use in the compositions are the beta-alkyloxy alkane sulfonates. These surfactants conform to the formula

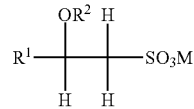

where R1 is a straight chain alkyl group having from about 6 to about 20 carbon atoms, R2 is a lower alkyl group having from about 1 to about 3 carbon atoms, alternatively 1 carbon atom, and M is a water-soluble cation as described hereinbefore.

Additional anionic surfactants suitable for use in the compositions include ammonium lauryl sulfate, ammonium laureth sulfate, ammonium laureth-1 sulfate, ammonium laureth-2 sulfate, ammonium laureth-3 sulfate, triethanolamine lauryl sulfate, triethanolamine laureth sulfate, triethanolamine laureth-1 sulfate, triethanolamine laureth-2 sulfate, triethanolamine laureth-3 sulfate, monoethanolamine lauryl sulfate, monoethanolamine laureth sulfate, diethanolamine lauryl sulfate, diethanolamine laureth sulfate, lauric monoglyceride sodium sulfate, sodium lauryl sulfate, sodium laureth sulfate, potassium lauryl sulfate, potassium laureth sulfate, sodium lauryl sarcosinate, sodium lauroyl sarcosinate, lauryl sarcosine, cocoyl sarcosine, ammonium cocoyl sulfate, ammonium lauroyl sulfate, sodium cocoyl sulfate, sodium lauroyl sulfate, potassium cocoyl sulfate, potassium lauryl sulfate, monoethanolamine cocoyl sulfate, monoethanolamine lauryl sulfate, sodium tridecyl benzene sulfonate, sodium dodecyl benzene sulfonate, sodium cocoyl isethionate, ammonium decyl sulfate, sodium decyl sulfate, ammonium undecyl sulfate, and ammonium undecyl sulfate and combinations thereof.

In one embodiment of the present invention, one or more of the surfactants is an alkyl sulfate. In one embodiment the one or more alkyl sulfates has an average moles of ethoxylation of from about 0.0 to about 1.9, in another embodiment the one or more alkyl sulfates has an average moles of ethoxylation of from about 0.0 to about 1.5, and in yet another embodiment the one or more alkyl sulfates has an average moles of ethoxylation of from about 0.0 to about 1.0. In one embodiment the one or more alkyl sulfates comprises an ammonium counter ion. Suitable examples of such surfactants with an ammonium counter ion include, but are not limited to, ammonium lauryl sulfate, ammonium laureth-1 sulfate, ammonium laureth-2 sulfate, and combinations thereof.

In one embodiment, one or more Group I surfactants are selected from alkyl sulfates with the following structure:

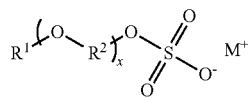

wherein $R^1$ is selected from C-linked monovalent substituents selected from the group consisting of substituted or unsubstituted, straight or branched alkyl or unsaturated alkyl systems comprising an average of 9.0 to 11.9 carbon atoms; $R^2$ is selected from the group consisting of C-linked divalent straight or branched alkyl systems comprising 2 to 3 carbon atoms; $M^+$ is a monovalent counterion selected from sodium, ammonium or protonated triethanolamine; and x is 0.0 to 3.0. In one embodiment, one or more of the alkyl sulfate surfactants according to the above structure comprise an average moles of ethoxylation of from about 0.0 to about 1.9, in another embodiment the alkyl sulfate surfactants according to the above structure comprise an average moles of ethoxylation of from about 0.0 to about 1.5, and in yet another embodiment the alkyl sulfate surfactants according to the above structure comprise an average moles of ethoxylation of from about 0.0 to about 1.0. Suitable examples include ammonium decyl sulfate, sodium decyl sulfate, ammonium undeceyl sulfate, sodium undeceyl sulfate, triethanolamine decyl sulfate, or triethanolamine undecyl sulfate. In one embodiment the anionic surfactant of the present invention includes ammonium undecyl sulfate.

Group II Surfactants

The Group II surfactants of the present invention include one or more amphoteric surfactants, zwitterionic surfactants, and/or combinations thereof. Suitable amphoteric or zwitterionic surfactants for use in the composition herein include those which are known for use in hair care or other personal care cleansing. Concentration of such amphoteric surfactants, zwitterionic surfactants and/or combinations thereof, range from about 1.0% to about 52.5% weight % of dry solids. Non limiting examples of suitable zwitterionic or amphoteric surfactants are described in U.S. Pat. No. 5,104, 646 (Bolich Jr. et al.), U.S. Pat. No. 5,106,609 (Bolich Jr. et al.).

Amphoteric surfactants suitable for use in the composition are well known in the art, and include those surfactants broadly described as derivatives of aliphatic secondary and tertiary amines in which the aliphatic radical can be straight or branched chain and wherein one of the aliphatic substituents contains from about 8 to about 18 carbon atoms and one contains an anionic group such as carboxy, sulfonate, sulfate, phosphate, or phosphonate. Suitable examples of such amphoteric surfactants include, but are not limited to, sodium cocaminopropionate, sodium cocaminodipropionate, sodium cocoamphoacetate, sodium cocoamphohydroxypropylsulfonate, sodium cocoamphopropionate, sodium cornamphopropionate, sodium lauraminopropionate, sodium lauroamphoacetate, sodium lauroamphohydroxypropylsulfonate, sodium lauroamphopropionate, sodium cornamphopropionate, sodium lauriminodipropionate, ammonium cocaminopropionate, ammonium cocaminodipropionate, ammonium cocoamphoacetate, ammonium cocoamphohydroxypropylsulfonate, ammonium cocoamphopropionate, ammonium cornamphopropionate, ammonium lauraminopropionate, ammonium lauroamphoacetate, ammonium lauroamphohydroxypropylsulfonate, ammonium lauroamphopropionate, ammonium cornamphopropionate, ammonium lauriminodipropionate, triethanonlamine cocaminopropionate, triethanonlamine cocaminodipropionate, triethanonlamine cocoamphoacetate, triethanonlamine cocoamphohydroxypropylsulfonate, triethanonlamine cocoamphopropionate, triethanonlamine cornamphopropionate, triethanonlamine lauraminopropionate, triethanonlamine lauroamphoacetate, triethanonlamine lauroamphohydroxypropylsulfonate, triethanonlamine lauroamphopropionate, triethanonlamine cornamphopropionate, triethanonlamine lauriminodipropionate, cocoamphodipropionic acid, disodium caproamphodiacetate, disodium caproamphoadipropionate, disodium capryloamphodiacetate, disodium capryloamphodipriopionate, disodium cocoamphocarboxyethylhydroxypropylsulfonate, disodium cocoamphodiacetate, disodium cocoamphodipropionate, disodium dicarboxyethylcocopropylenediamine, disodium laureth-5 carboxyamphodiacetate, disodium lauriminodipropionate, disodium lauroamphodiacetate, disodium lauroamphodipropionate, disodium oleoamphodipropionate, disodium PPG-2-isodecethy-7 carboxyamphodiacetate, lauraminopropionic acid, lauroamphodipropionic acid, lauryl aminopropylglycine, lauryl diethylenediaminoglycine, and combinations thereof.

In one embodiment, the amphoteric surfactant is a surfactant according to the following structure:

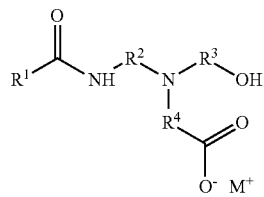

wherein R1 is a C-linked monovalent substituent selected from the group consisting of substituted alkyl systems comprising 9 to 15 carbon atoms, unsubstituted alkyl systems comprising 9 to 15 carbon atoms, straight alkyl systems comprising 9 to 15 carbon atoms, branched alkyl systems comprising 9 to 15 carbon atoms, and unsaturated alkyl systems comprising 9 to 15 carbon atoms; R2, R3, and R4 are each independently selected from the group consisting of C-linked divalent straight alkyl systems comprising 1 to 3 carbon atoms, and C-linked divalent branched alkyl systems comprising 1 to 3 carbon atoms; and M+ is a monovalent counterion selected from the group consisting of sodium, ammonium and protonated triethanolamine Specific examples of suitable surfactants include sodium cocoamphoacetate, sodium cocoamphodiacetate, sodium lauroamphoacetate, sodium lauroamphodiacetate, ammonium lauroamphoacetate, ammonium cocoamphoacetate, triethanolamine lauroamphoacetate, and triethanolamine cocoamphoacetate.

Zwitterionic surfactants suitable for use in the composition are well known in the art, and include those surfactants broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. Suitable zwitterionic surfactants include, but are not limited to, cocamidoethyl betaine, cocamidopropylamine oxide, cocamidopropyl betaine, cocamidopropyl dimethylaminohydroxypropyl hydrolyzed collagen, cocamidopropyldimonium hydroxypropyl hydrolyzed collagen, cocamidopropyl hydroxysultaine, cocobetaineamido amphopropionate, coco-betaine, coco-hydroxysultaine, coco/oleamidopropyl betaine, coco-sultaine, lauramidopropyl betaine, lauryl betaine, lauryl hydroxysultaine, lauryl sultaine, and combinations thereof.

Optional Surfactants

The compositions of the present invention may further comprise additional surfactants for use in combination with the anionic detersive surfactant component described hereinbefore. Suitable optional surfactants include nonionic and cationic surfactants. Any such surfactant known in the art for use in hair or personal care products may be used, provided that the optional additional surfactant is also chemically and physically compatible with the essential components of the composition, or does not otherwise unduly impair product performance, aesthetics or stability. The concentration of the optional additional surfactants in the composition may vary with the cleansing or lather performance desired, the optional surfactant selected, the desired product concentration, the presence of other components in the composition, and other factors well known in the art.

Non limiting examples of other anionic, zwitterionic, amphoteric or optional additional surfactants suitable for use in the compositions are described in McCutcheon's, Emulsifiers and Detergents, 1989 Annual, published by M. C. Publishing Co., and U.S. Pat. Nos. 3,929,678, 2,658,072; 2,438,091; 2,528,378.

Plasticizer

The dissolvable solid articles of the present invention may further comprise a water soluble plasticizing agent suitable for use in personal care compositions. The water soluble plasticizer can be included in the article at a level of from about 0.1% to about 25% by weight of the article. Non-limiting examples of suitable plasticizing agents include polyols, copolyols, and polyesters. Examples of useful polyols include, but are not limited to, glycerin, diglycerin, propylene glycol, ethylene glycol, butylene glycol, pentylene glycol, polyethylene glycol (200-600), polyhydric low molecular weight alcohols (e.g., C2-C8 alcohols); mono di- and oligo-saccharides such as fructose, glucose, sucrose, maltose, lactose, and high fructose corn syrup solids.

Optional Ingredients

The dissolvable solid article may further comprise other optional ingredients that are known for use or otherwise useful in compositions, provided that such optional materials are compatible with the selected essential materials described herein, or do not otherwise unduly impair product performance.

Such optional ingredients are most typically those materials approved for use in cosmetics and that are described in reference books such as the CTFA Cosmetic Ingredient Handbook, Second Edition, The Cosmetic, Toiletries, and Fragrance Association, Inc. 1988, 1992.

Emulsifiers suitable as an optional ingredient herein include mono- and di-glycerides, fatty alcohols, polyglycerol esters, propylene glycol esters, sorbitan esters and other emulsifiers known or otherwise commonly used to stabilized air interfaces, as for example those used during preparation of aerated foodstuffs such as cakes and other baked goods and confectionary products, or the stabilization of cosmetics such as hair mousses.

Further non-limiting examples of such optional ingredients include preservatives, perfumes or fragrances, coloring agents or dyes, conditioning agents, hair bleaching agents, thickeners, moisturizers, emollients, pharmaceutical actives, vitamins or nutrients, sunscreens, deodorants, sensates, plant extracts, nutrients, astringents, cosmetic particles, absorbent particles, adhesive particles, hair fixatives, fibers, reactive agents, skin lightening agents, skin tanning agents, anti-dandruff agents, perfumes, exfoliating agents, acids, bases, humectants, enzymes, suspending agents, pH modifiers, hair colorants, hair perming agents, pigment particles, anti-acne agents, anti-microbial agents, sunscreens, tanning agents, exfoliation particles, hair growth or restorer agents, insect repellents, shaving lotion agents, co-solvents or other additional solvents, and similar other materials.

Additional anti-bacterial actives can be added at a level of 0.15% to about 1.5%. Such anti-bacterial actives are, for example: CLIMBAZOLE; Piroctone Olamine; CHLORHEXIDINE; CHLORHEXIDINE DIHYDROCHLORIDE; HEXAMIDINE DIISETHIONATE; CHLORPHENESIN; POTASSIUM SALICYLATE; ZINC PYRITHIONE; PHENOXYETHANOL; and combinations thereof.

Dissolvable Solid Articles

The dissolvable solid article has a pH of from about 3 to about 5.1, alternatively from about 3.5 to about 4.9, alternatively from about 3.8 to about 4.8, when dissolved with 30 parts water to 1 part of the dissolvable solid article (weight basis).

The term "solid" as used herein refers to the ability of an article to substantially retain its shape (i.e., without any visible change in its shape) at 20° C. and under the atmospheric pressure, when no external force is applied thereto.

The term "flexible" as used herein refers to the ability of an article to withstand stress without breakage or significant fracture when it is bent at 90° along a center line perpendicular to its longitudinal direction. Alternatively, such article can undergo significant elastic deformation and is characterized by a Young's Modulus of no more than 5 GPa, alternatively no more than 1 GPa, alternatively no more than 0.5 GPa, alternatively no more than 0.2 GPa.

The dissolvable solid article useful herein is capable of dissolving in the liquid, especially aqueous carrier, more specifically water. Water can be added to 1 part of the article, from about 1 100 parts, alternatively from about 5 to about 50 parts, alternatively from about 10 to about 40 parts.

As used herein, "dissolvable" means that the dissolvable solid article is completely soluble in water or it provides a uniform dispersion upon mixing in water according to the hand dissolution test. The dissolvable solid article has a hand dissolution value of from about 0 to about 30 strokes, alternatively from about 0 to about 25 strokes, alternatively from about 0 to about 20 strokes, and alternatively from about 0to about 15 strokes, as measured by the Hand Dissolution Method. "0 stroke" mean, just by adding water, the article is dissolved without any shear or hand stroke.

The dissolvable solid article is alternatively porous, and can be characterized by a density ranging from 0.050 g/cm$^3$ to about 0.380 g/cm$^3$, alternatively from 0.06 grams/cm$^3$ to 0.3 grams/cm$^3$, alternatively from 0.07 grams/cm$^3$ to 0.2 grams/cm$^3$, alternatively from 0.08 grams/cm$^3$ to 0.15 grams/cm$^3$. The dissolvable solid structure of the present invention can be provided in the form of a dissolvable solid article comprising one or more flexible, dissolvable, porous sheets, wherein each of said two or more sheets is characterized by being an open-celled foam, a fibrous structure, and the like. The porous sheets can be optionally bonded together via a bonding means (e.g., heat, moisture, ultrasonic, pressure, and the like).

The term "open celled foam" or "open cell pore structure" as used herein refers to a solid, interconnected, polymer-containing matrix that defines a network of spaces or cells that contain a gas, typically a gas (such as air), while maintaining the physical strength and cohesiveness of the solid. The interconnectivity of the structure may be described by a Percent Open Cell Content, which is measured by Test 1 disclosed hereinafter. The dissolvable solid article useful herein can be characterized by a Percent Open Cell Content of from 80% to 100%.

Hand Dissolution Test Method
Materials Needed:
Dissolvable solid structures to be tested: 3-5 dissolvable solid structure s (finished product samples) are tested so that an average of the number of strokes for each if the individual dissolvable solid structure samples is calculated and recorded as the Average Hand Dissolution value for the dissolvable solid structure. For this method, the entire consumer saleable or consumer use dissolvable solid structure is tested. If the entire consumer saleable or consumer use dissolvable solid structure has a footprint greater than 5 cm², then first cut the dissolvable solid structure to have a footprint of 5 cm².
Nitrile Gloves
5 ml syringe
Plastic Weigh boat (~3M×3 in)
50 mL Glass beaker
Water (City of Singapore Water or equivalent having the following properties: Total Hardness=64 mg/L as CaCO2; Calcium content=23 mg/L; Magnesium content=1.58 mg/L; Phosphate content=0.017 mg/L)
Water used is 3 gpg hardness and 23° C.+/−2° C.
Protocol:
Add 10 mL of water to glass beaker.
Cool water in beaker until water is at a temperature of 23° C.+/−2° C.
Transfer 4 mL of the water from the beaker into the weigh boat via the syringe.
Within 10 seconds of transferring the water to the weigh boat, place dissolvable solid structure sample in palm of gloved hand (hand in cupped position in non-dominant hand to hold dissolvable solid structure sample).
Using dominant hand, add water quickly from the weigh boat to the dissolvable solid structure sample and allow to immediately wet for a period of 5-10 seconds.
Rub with opposite dominant hand (also gloved) in 2 rapid circular strokes.
Visually examine the dissolvable solid structure sample in hand after the 2 strokes. If dissolvable solid structure sample is completely dissolved, record number of strokes=2 Dissolution Strokes. If not completely dissolved, rub remaining dissolvable solid structure sample for 2 more circular strokes (4 total) and observe degree of dissolution. If the dissolvable solid structure sample contains no solid pieces after the 2 additional strokes, record number of strokes=4 Dissolution Strokes. If after the 4 strokes total, the dissolvable solid structure sample still contains solid pieces of un-dissolved dissolvable solid structure sample, continue rubbing remaining dissolvable solid structure sample in additional 2 circular strokes and check if there are any remaining solid pieces of dissolvable solid structure sample after each additional 2 strokes until dissolvable solid structure sample is completely dissolved or until reaching a total of 30 strokes, whichever comes first. Record the total number of strokes. Record 30 Dissolution Strokes even if solid dissolvable solid structure sample pieces remain after the maximum of 30 strokes.
Repeat this process for each of the additional 4 dissolvable solid structure samples.
Calculate the arithmetic mean of the recorded values of Dissolution Strokes for the 5 individual dissolvable solid structure samples and record as the Average Hand Dissolution Value for the dissolvable solid structure. The Average Hand Dissolution Value is reported to the nearest single Dissolution Stroke unit.

Test 1: Percent Open Cell Content of the Sheet Article

The Percent Open Cell Content is measured via gas pycnometry. Gas pycnometry is a common analytical technique that uses a gas displacement method to measure volume accurately. Inert gases, such as helium or nitrogen, are used as the displacement medium. A sample of the solid sheet article of the present invention is sealed in the instrument compartment of known volume, the appropriate inert gas is admitted, and then expanded into another precision internal volume. The pressure before and after expansion is measured and used to compute the sample article volume.

ASTM Standard Test Method D2856 provides a procedure for determining the percentage of open cells using an older model of an air comparison pycnometer. This device is no longer manufactured. However, one can determine the percentage of open cells conveniently and with precision by performing a test which uses Micromeritics' AccuPyc Pycnometer. The ASTM procedure D2856 describes 5 methods (A, B, C, D, and E) for determining the percent of open cells of foam materials. For these experiments, the samples can be analyzed using an Accupyc 1340 using nitrogen gas with the ASTM foampyc software. Method C of the ASTM procedure is to be used to calculate to percent open cells. This method simply compares the geometric volume as determined using calipers and standard volume calculations to the open cell volume as measured by the Accupyc, according to the following equation:

Open cell percentage=Open cell volume of sample/ Geometric volume of sample*100

It is recommended that these measurements be conducted by Micromeretics Analytical Services, Inc. (One Micromeritics Dr, Suite 200, Norcross, GA 30093). More information on this technique is available on the Micromeretics Analytical Services web sites or published in "Analytical Methods in Fine particle Technology" by Clyde Orr and Paul Webb.

The dissolvable solid articles can be characterized by Overall Average Pore Size of from 100 μm to 2000 μm, as measured by the Micro-CT method described in Test 2 hereinafter. The Overall Average Pore Size defines the porosity of the dissolvable solid article.

The dissolvable solid articles can be characterized by an Average Cell Wall Thickness or Average Filament Diameter of from 1 μm to 200 μm, alternatively from 10 μm to 100 μm, alternatively from 20 μm to 80 μm; still alternatively from about 25 μm to 60 μm, as measured by Test 2 hereinafter.

Test 2: Micro-Computed Tomographic (μCT) Method for Determining Overall or Regional Average Pore Size and Average Cell Wall Thickness of the Open Cell Foams (OCF)

Porosity is the ratio between void-space to the total space occupied by the OCF. Porosity can be calculated from μCT scans by segmenting the void space via thresholding and determining the ratio of void voxels to total voxels. Similarly, solid volume fraction (SVF) is the ratio between solid-space to the total space, and SVF can be calculated as the ratio of occupied voxels to total voxels. Both Porosity and SVF are average scalar-values that do not provide structural information, such as, pore size distribution in the height-direction of the OCF, or the average cell wall thickness of OCF struts.

To characterize the 3D structure of the OCFs, samples are imaged using a μCT X-ray scanning instrument capable of acquiring a dataset at high isotropic spatial resolution. One example of suitable instrumentation is the SCANCO system model 50 μCT scanner (Scanco Medical AG, Brüttisellen, Switzerland) operated with the following settings: energy level of 45 kVp at 133 μA; 3000 projections; 15 mm field of view; 750 ms integration time; an averaging of 5; and a voxel size of 3 μm per pixel. After scanning and subsequent data reconstruction is complete, the scanner system creates a 16 bit data set, referred to as an ISQ file, where grey levels reflect changes in x-ray attenuation, which in turn relates to material density. The ISQ file is then converted to 8 bit using a scaling factor.

Scanned OCF samples are normally prepared by punching a core of approximately 14 mm in diameter. The OCF punch is laid flat on a low-attenuating foam and then mounted in a 15 mm diameter plastic cylindrical tube for scanning Scans of the samples are acquired such that the entire volume of all the mounted cut sample is included in the dataset. From this larger dataset, a smaller sub-volume of the sample dataset is extracted from the total cross section of the scanned OCF, creating a 3D slab of data, where pores can be qualitatively assessed without edge/boundary effects.

To characterize pore-size distribution in the height-direction, and the strut-size, Local Thickness Map algorithm, or LTM, is implemented on the subvolume dataset. The LTM Method starts with a Euclidean Distance Mapping (EDM) which assigns grey level values equal to the distance each void voxel is from its nearest boundary. Based on the EDM data, the 3D void space representing pores (or the 3D solid space representing struts) is tessellated with spheres sized to match the EDM values. Voxels enclosed by the spheres are assigned the radius value of the largest sphere. In other words, each void voxel (or solid voxel for struts) is assigned the radial value of the largest sphere that that both fits within the void space boundary (or solid space boundary for struts) and includes the assigned voxel.

The 3D labelled sphere distribution output from the LTM data scan can be treated as a stack of two dimensional images in the height-direction (or Z-direction) and used to estimate the change in sphere diameter from slice to slice as a function of OCF depth. The strut thickness is treated as a 3D dataset and an average value can be assessed for the whole or parts of the subvolume. The calculations and measurements were done using AVIZO Lite (9.2.0) from Thermo Fisher Scientific and MATLAB (R2017a) from Mathworks.

The dissolvable solid articles can be characterized by a Specific Surface Area of from 0.03 $m^2/g$ to 0.25 $m^2/g$, alternatively from 0.04 $m^2/g$ to 0.22 $m^2/g$, alternatively from 0.05 $m^2/g$ to 0.2 $m^2/g$, alternatively from 0.1 $m^2/g$ to 0.18 $m^2/g$. as measured by Test 3 described hereinafter. The Specific Surface Area of the solid sheet of the present invention may be indicative of its porosity and may impact its dissolution rate, e.g., the greater the Specific Surface Area, the more porous the sheet and the faster its dissolution rate.

Test 3: Specific Surface Area of the Sheet Article

The Specific Surface Area of the flexible, porous, dissolvable solid sheet article is measured via a gas adsorption technique. Surface Area is a measure of the exposed surface of a solid sample on the molecular scale. The BET (Brunauer, Emmet, and Teller) theory is the most popular model used to determine the surface area and is based upon gas adsorption isotherms. Gas Adsorption uses physical adsorption and capillary condensation to measure a gas adsorption isotherm. The technique is summarized by the following steps; a sample is placed in a sample tube and is heated under vacuum or flowing gas to remove contamination on the surface of the sample. The sample weight is obtained by subtracting the empty sample tube weight from the combined weight of the degassed sample and the sample tube. The sample tube is then placed on the analysis port and the analysis is started. The first step in the analysis process is to evacuate the sample tube, followed by a measurement of the free space volume in the sample tube using helium gas at liquid nitrogen temperatures. The sample is then evacuated a second time to remove the helium gas. The instrument then begins collecting the adsorption isotherm by dosing krypton gas at user specified intervals until the requested pressure measurements are achieved. Samples may then analyzed using an ASAP 2420 with krypton gas adsorption. It is recommended that these measurements be conducted by Micromeretics Analytical Services, Inc. (One Micromeritics Dr, Suite 200, Norcross, GA 30093). More information on this technique is available on the Micromeretics Analytical Services web sites or published in a book, "Analytical Methods in Fine particle Technology", by Clyde Orr and Paul Webb.

The dissolvable solid articles can be characterized by a final moisture content of from 0.5% to 25%, alternatively from 1% to 20%, alternatively from 3% to 10%, by weight of said article as measured by Test 4 hereinafter. An appropriate final moisture content in the resulting solid sheet may ensure the desired flexibility/deformability of the sheet, as well as providing soft/smooth sensory feel to the consumers. If the final moisture content is too low, the sheet may be too brittle or rigid. If the final moisture content is too high, the sheet may be too sticky, and its overall structural integrity may be compromised.

Test 4: Final Moisture Content of the Sheet Article

Final moisture content of the solid sheet article of the present invention is obtained by using a Mettler Toledo HX204 Moisture Analyzer (S/N B706673091). A minimum of 1 g of the dried sheet article is placed on the measuring tray. The standard program is then executed, with additional program settings of 10 minutes analysis time and a temperature of 110° C.

Product

The dissolvable solid articles can be any product including, for example, personal care products, home care products, surface cleaning products, general cleaning products. Alternatively, the product is a personal care product. Such personal products include, for example, personal cleansing products such as body, facial and/or hand cleansing products, skin care products such as Lotion, facial mist, gel, cream, hair care products such as shampoos and conditioners.

Method of Use

The method of use of the dissolvable solid article may comprise the steps of: a) applying an effective amount of the dissolvable porous solid to the hand, b) wetting the dissolvable porous solid with water and rubbing to dissolve the solid, c) applying the dissolved material to the subject such as hair and/or skin, and d) rinsing the dissolved material from the subject using water.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention. Where applicable, ingredients are identified by chemical or CTFA name, or otherwise defined below.

Dissolvable solid article composition

| Ingredient Name | CEx. i | CEx. ii | Ex. 1 |
|---|---|---|---|
| Water | 5.84 | 5.49 | 5.61 |
| Glycerin | 6.58 | 6.19 | 6.33 |
| Sodium lauramidopropyl betaine | 7.23 | 6.80 | 6.95 |
| Sodium Methyl Cocoyl Taurate | 19.23 | 18.08 | 18.50 |
| Polyvinyl Alcohol (BP-17 having 86-90% degree of hydrolysis, Approximate MW(weight average) = 70,000-120,000 daltons, available from Liwei Chemical Co. Ltd., China) | 21.41 | 20.13 | 20.59 |
| Sodium Cocoyl Isethionate | 10.84 | 10.19 | 10.43 |
| Sodium Cocoyl Glutamate | 10.84 | 10.19 | 10.43 |
| EDTA | | 1.00 | 1.00 |
| Sodium Benzoate | | 0.50 | 0.50 |
| Potassium Sorbate | | 0.50 | 0.50 |
| Symsave H (Hydroxyacetophenone) | | 2.00 | 2.00 |
| Symdiol 68 (50:50 blend of 1,2-Hexanediol and 1,2-Octanediol) | | 1.00 | 1.00 |
| salicylic acid | | | 0.50 |
| Sodium citrate | 7.51 | 7.51 | 5.00 |
| Citric acid | 10.80 | 10.80 | 11.00 |
| | 100 | 100 | 100 |
| C4 Result (gram negative) | −16.15 | −11.54 | 69.28 |
| pH | 4.75 | 4.77 | 4.26 |

Dissolvable solid article composition

| Ingredient Name | Ex. 2 | Ex. 3 | CEx.iii | Ex. 4 | Ex. 5 | Ex, 6 | Ex. 7 |
|---|---|---|---|---|---|---|---|
| Water | 10.00 | 10.00 | 10.00 | 10.00 | 10.00 | 10.00 | 10.00 |
| Glycerin | 7.55 | 7.65 | 8.22 | 8.30 | 8.21 | 8.22 | 8.12 |
| Sodium lauroamphoacetate | 9.06 | 9.18 | 9.87 | 9.97 | 9.86 | 9.87 | 9.75 |
| Sodium Laureth ethoxy (1) sulfate (SLE1S) | 38.85 | 39.34 | 42.30 | 42.72 | 42.25 | 42.31 | 41.79 |
| Polyvinyl Alcohol BP-17 having 86-90% degree of hydrolysis, Approximate MW(weight average) = 70,000-120,000 daltons, available from Liwei Chemical Co. Ltd., China | 19.81 | 20.06 | 21.57 | 21.78 | 21.55 | 21.58 | 21.32 |
| Denatonium Benzoate | 0.012 | 0.012 | 0.013 | 0.013 | 0.013 | 0.013 | 0.013 |
| Perfume | 1.17 | 1.18 | 1.27 | 1.28 | 1.27 | 1.27 | 1.25 |
| Sodium Benzoate | 0.48 | 0.48 | 0.45 | 0.45 | 0.44 | 0.44 | 0.44 |
| EDTA 2Na | 0.97 | 0.97 | 0.90 | 0.89 | 0.89 | 0.89 | 0.88 |
| Salicylic acid | 0.48 | | 0.45 | 0.45 | 0.44 | 0.44 | 0.44 |
| Symdiol 68 (50:50 blend of 1,2-Hexanediol and 1,2-Octanediol) | 0.97 | 0.48 | 0.90 | 0.89 | 0.89 | 0.89 | 0.88 |
| Potassium Sorbate | | | 0.45 | | | | |
| Symsave H (Hydroxyacetophenone) | | | 0.90 | | | | |
| Sodium Citrate | 2.90 | 2.90 | | | | | |
| Citric Acid | 7.74 | 7.74 | 2.70 | | 2.66 | 2.67 | 2.63 |
| Lactic acid | | | | 2.68 | | | |
| 6N HCl | | | | 0.57 | | | |
| Sorbic Acid | | | | | 1.52 | | |
| Benzoic Acid | | | | | | | 2.48 |
| Phytic Acid | | | | | | 1.41 | |
| C4 Result (gram negative) | 99.99 | 97.96 | −4.59 | 99.59 | 73.68 | 84.36 | 98.36 |
| pH | 4.25 | 4.25 | 5.52 | 4.48 | 5.02 | 4.72 | 4.68 |

C4 Result (Gram Negative)
Preparation of Bacterial Suspension

A $1\times10^6\sim9\times10^6$ CFU/mL *S. aureus* ATCC6538 or *E. coli* ATCC25922 bacterial suspension was prepared by washing off the bacteria from agar plate with 0.03M Phosphate Buffered Solution (PBS).

Preparation of Control Sample 5 mL Saline solution (0.85% w/v NaCl) was used as a Control sample for the test.

Preparation of Test Samples

Dissolve and dilute 1 part of the composition in the above table with 30 parts of water to prepare Test sample.

Test

100 µl of the bacterial suspension was added to 5 mL of the sample to achieve $1\times10^4\sim9\times10^4$ CFU/mL to make a mixture, and the mixture was vortexed and stand for 2 min. Then, 1.0 mL of the mixture was transferred into a test tube containing 9.0 mL of 0.03M PBS and mixed to diluted. Serial dilutions were performed to dilute the concentration of the mixture to 10000 times with 0.03M PBS. The serially diluted mixture was plated by adding 1.0 mL of such serially diluted mixture into 2 petri dishes.

Molten (~20 mL, 40~45° C.) Tryptic Soy Agar (TSA) was poured into the petri dish and swirled to mix. The agar was allowed to cool and harden before turning over and incubated at 35±2° C. for 48 h.

Bactericidal rate is calculated following below:
where:

$$X_4 = \frac{(A-B)}{A} \times 100\%$$

$X_4$=bactericidal rate, %
A=mean bacteria count on control sample
B=mean bacteria count on tested sample Criteria for Evaluation If the bactericidal rate is ≥50~90%, it can be reported that the tested products have bacteriostatic effect.

If the bactericidal rate is ≥90%, it can be reported that the tested products have strong bacteriostatic effect.

The compositions of Ex. 1 to Ex. 7 are examples of the present invention. The compositions of CEx. i to CEx.iii are comparative examples. The composition CEx.i does not contain anti-bacterial active, the composition CEx. ii contains higher % of citric acid and its salt, and the composition of CEx. iii has a higher pH.

The compositions of Ex. 1 to Ex. 7 as examples of the present invention provide anti-bacterial benefit even after dissolution of the article, while controlling the concentration of anti-bacterial active ingredient in the solid articles. The compositions of CEx. i to CEx.iii as comparative examples do not provide anti-bacterial benefit.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A dissolvable solid article, comprising by weight of the article:
   a. from about 10% to about 50% of one or more water soluble polymers;
   b. from about 20% to about 80% of one or more surfactants comprising:
      i. an anionic surfactant comprising sodium laureth sulfate;
      ii. one or more Group II surfactants chosen from zwitterionic surfactants and/or amphoteric surfactants;
   c. from about 0.5% to about 2% of an ethylenediaminetetraacetic acid;
   d. from about 0.1% to about 4% of salicylic acid;
   e. from about 1% to about 6% of one or more non-aromatic organic alpha hydroxy acid and salts thereof chosen from citric acid, lactic acid, malic acid, tartaric acid, gluconic acid, glyceric acid, xylonic acid, galactaric acid, or mixtures thereof;
   wherein when the dissolvable solid article is dissolved with 30 parts water to 1 part of the dissolvable solid article to form a dilution, the dilution comprises a pH of from about 3.8 to about 4.8;
   wherein the solid article comprises an open cell pore structure;
   wherein the solid article is a personal cleansing product, shampoo, and/or conditioner;
   wherein the article comprises a bacteriacidal rate ≥90%.

2. The dissolvable solid article of claim 1, wherein the dilution comprises a pH of from about 3.8 to about 4.

3. The dissolvable solid article of claim 1, further comprising from about 0.1% to about 2.0% of one or more diols having an average molecular weight of from about 90 to about 500 daltons and a weighted log P value at pH 4 of from about −1 to about 12.

4. The dissolvable solid article of claim 1, wherein the dissolvable solid article comprises two or more flexible, dissolvable, porous sheets.

5. The dissolvable solid article of claim 1, wherein the dissolvable solid article comprises a density ranging from about 0.050 g/cm$^3$ to about 0.380 g/cm$^3$.

6. The dissolvable solid article of claim 1, wherein the article comprises from about 80% to about 100% Open Cell Content.

7. The dissolvable solid article of claim 1, wherein the article comprises a hand dissolution value of about 0 to about 20 strokes.

8. The dissolvable solid article of claim 1, wherein the article comprises a hand dissolution value of about 0 to about 15 strokes.

9. The dissolvable solid article of claim 1, wherein the non-aromatic organic alpha hydroxy acids and salts thereof are chosen from citric acid, lactic acid, gluconic acid, or mixtures thereof.

10. The dissolvable solid article of claim 3, wherein the one or more diols are chosen from 1,2-Hexanediol, and/or 1,2-Octanediol.

11. The dissolvable solid article of claim 10, wherein the composition comprises 1,2-Hexanediol and 1,2-Octanediol.

12. The dissolvable solid article of claim 1, wherein the one or more water soluble polymers are chosen from polyvinyl alcohol, polyvinylpyrrolidones, polyalkylene oxides, starch and starch derivatives, pullulan, gelatin, hydroxypropylmethylcelluloses, methylcelluloses, carboxymethycelluloses, or mixtures thereof.

13. The dissolvable solid article of claim 1, wherein the one or more water soluble polymers are chosen from polyvinyl alcohol, polyvinylpyrrolidones, or mixtures thereof.

14. A dissolvable solid article, comprising by weight of the article:
   a. from about 10% to about 50% of one or more water soluble polymers; wherein the one or more water soluble polymers are chosen from polyvinyl alcohol, polyvinylpyrrolidones, or mixtures thereof;
   b. from about 20% to about 80% of a one or more surfactants comprising:
      i. an anionic surfactant comprising sodium laureth sulfate;
      ii. one or more Group II surfactants chosen from zwitterionic surfactants and/or amphoteric surfactants;
   c. from about 0.5% to about 2% of an ethylenediaminetetraacetic acid;
   d. from about 0.1% to about 6% salicylic acid;
   e. from about 0.1% to about 18% of one or more non-aromatic organic alpha hydroxy acid and salts thereof; wherein the non-aromatic organic alpha hydroxy acids and salts thereof are chosen from citric acid, lactic acid, gluconic acid, or a mixtures thereof;
   f. sodium benzoate;
   g. 1,2-Hexanediol and/or 1,2-Octanediol;
      wherein when the dissolvable solid article is dissolved with 30 parts water to 1 part of the dissolvable solid article to form a dilution, the dilution comprises a pH of from about 3 to about 5.1;
      wherein the solid article comprises an open cell pore structure;
      wherein the solid article is a personal cleansing product, shampoo, and/or conditioner;
      wherein the article comprises a bacteriacidal rate ≥90%.

15. The dissolvable solid article of claim 14,
   wherein the one or more water soluble polymers comprise polyvinyl alcohol;
   wherein the non-aromatic organic alpha hydroxy acids and salts thereof are chosen from citric acid, lactic acid, or mixtures thereof.

* * * * *